United States Patent [19]

Solodar

[11] 4,215,065

[45] Jul. 29, 1980

[54] ACID SEPARATION

[75] Inventor: A. John Solodar, St. Louis, Mo.

[73] Assignee: Monsanto Company, St. Louis, Mo.

[21] Appl. No.: 451

[22] Filed: Jan. 2, 1979

[51] Int. Cl.$^2$ ............................. C11C 1/04; C11C 3/02
[52] U.S. Cl. .............................. 260/415; 260/410.9 R;
   260/413; 260/421; 260/410; 560/191; 560/218;
   560/233; 560/248; 562/522; 562/593; 562/600
[58] Field of Search ................. 260/410.9 D, 410.9 E,
   260/410.9 C, 410, 413 R, 413 C, 415, 421;
   560/233, 248, 191, 218; 562/600, 593, 522

[56] References Cited

U.S. PATENT DOCUMENTS

| | | | |
|---|---|---|---|
| 2,238,442 | 4/1941 | Drew | 260/415 |
| 2,681,356 | 6/1954 | Wiese | 260/415 X |
| 2,844,612 | 6/1958 | Rottig | 260/410.9 C |
| 3,668,249 | 6/1972 | Fenton | 260/410.9 C |

OTHER PUBLICATIONS

Loening et al., J. Amer. Chem. Soc., 74 3929, (1952).

*Primary Examiner*—John F. Niebling
*Attorney, Agent, or Firm*—Joseph D. Kennedy; James W. Williams, Jr.

[57] ABSTRACT

Differential esterification or hydrolysis is utilized to effect separations of isomeric acids or esters.

16 Claims, No Drawings

ACID SEPARATION

The present invention is concerned with a method of separating acids in accordance with their structure in order to provide acid products with either greater linearity, or with more branching.

BACKGROUND OF THE INVENTION

Fatty acids are commercial commodities available from a number of natural sources. Similar synthetic acids can be synthesized from olefins by hydrocarboxylation of the olefins over catalysts, and also by hydroesterification of olefins over catalysts, followed by hydrolysis. It happens that such procedures often result in acids of varying linearity, i.e. the product may contain a quantity of linear, that is normal, acids along with acids of branched structure. The degree of normality obtained can be influenced to some extent by reaction conditions, as well as by the olefin feed stock, i.e. the amount of branching and the presence of terminal rather than internal unsaturation. However, there are generally limits to normality obtainable by reaction modifications, and there is the matter of availability and cost of olefin feed stock, or the expense of distillation or other procedures to obtain a more suitable feed stock. Moreover, a range of acids is often produced, e.g. over a carbon atom range of 11 to 13 carbon atoms. Because of the range of boiling points resulting from molecular weight differences, it is often impractical to use distillation as a means of separating the acids in accordance with linearity.

SUMMARY OF THE INVENTION

The present invention utilizes the differential hydrolysis rate of isomeric carboxylic acid esters as a means of effecting their separation. Conversely, the invention can utilize the differential esterification rate of the acids for such purpose, or some combination of the two procedures. Ordinarily complete separation is not necessary, but a mixture of isomers is enriched with respect to desired isomers. In particular applications acid mixtures varying over a range of carbon numbers, as well as containing different isomers, are partial hydrolyzed or esterified and the resulting mixture of acids and esters is separated by distillation to give esters and acids which are respectively enriched in different isomeric forms. The process provides a degree of control over the linearity of synthetic fatty acids obtained by hydrocarboxylation or hydroesterification of olefin feed stocks, by a procedure apart from the production reaction itself or modification of the feed stock. The differential hydrolysis or esterification can be employed with crude mixtures containing aldehydes, hydrocarbons or other impurities, along with mixtures of various acids, or with isolated mixtures of acids or isomers of a single acid. Ordinary hydrolysis or esterification conditions can be used, including thermal procedures, or acid or base catalyzed procedures, etc. The separation can be used in conjunction with, or as part of, a hydroesterification procedure to convert olefins to esters and then to obtain separate acid fractions enriched respectively in linear and branched structures.

DETAILED DISCLOSURE OF THE INVENTION

Hydrolysis-Esterification can be represented:

in which R and R' represent alkyl groups. This is an equilibrium reaction which can be driven in either direction by adjustment of concentration of the components. For example, the hydrolysis reaction can be promoted by providing or maintaining high concentrations of the ester and or water, and also by having only low concentrations of either or both of the acid and the alcohol present, e.g. by removing one or both of these products as produced during the hydrolysis. It happens that in the indicated reaction, the rate, of both hydrolysis and esterification, is affected by the structure of the alkanoic acid, i.e., by whether R is of linear or branched structure, and the degree of branching. It has been found that if a mixture of alkanoic acids of varying chain structure is subjected to differential hydrolysis, the normal acid esters hydrolyze more rapidly than the branched acids, and a reaction mixture is obtained in which the acid form contains a higher percentage of the normal acid moiety than is found in the ester form. By differential hydrolysis is meant hydrolysis short of completion so that the effect of the relative rates upon product is obtained. If the ester were 100% hydrolyzed, of course, the relative amounts of normal and branched acids in the acid form would be the same as present in the ester. Differential hydrolysis also means not continuing the hydrolysis to equilibrium, as the equilibrium position of a mixture of acid-esters will be approximately the same. By equilibrium is meant that the hydrolysis and esterification reactions are proceeding at the same rate, so that there is no net change in the acid and ester content. In practice it will usually be desirable to remove one or more products during the reaction, and therefore equilibrium considerations alone do not prevent approaching 100% conversion.

The present invention can be employed with any mixtures of carboxylic acids or esters having different hydrolysis rates. Such mixtures can include alkanoic acids of up to twenty or so carbon atoms, or even higher alkanoic acids, although of less interest, The carboxylic acids constituting or resembling the natural fatty acids and being hydrocarbon in structure, except for the carboxy group, are an important group of such acids for use herein. Such acids with four or more carbon atoms can exist in isomeric forms which lead to different hydrolysis rates. Many of the carboxylic acid mixtures of interest will be saturated carboxylic acids, e.g. alkanoic acids, but mixtures including unsaturated acids can be used, e.g. with one or more olefinic bonds. Similarly, the acids can have one or more substituents which do not unduly interfere with the hydrolysis, such as hydroxyl groups, ether groups, halogens, etc. The invention will have particular application to separations in soap or detergent ranges of acids, e.g. acids of 8 to 16 or so carbon atoms, or more narrowly, 10 to 14 carbon atoms. It can also be employed with mixtures of acids or esters or potential use for plasticizers including for example, acids of six to eight carbon atoms. While the exemplifications herein for the most part concern variations in aliphatic chain structure, the invention is applicable to separation of isomeric aromatic carboxylic acids having different hydrolysis rates.

The hydrolysis and esterification rates of carboxylic acids vary with both the number of carbon atoms, and their position. Esterification rates with methanol for some lower carboxylic acids have been reported (Loening et al, J. Amer. Chem. Soc. 74, 3929 (1952)) and are presented on a relative rate bias as follows:

| | |
|---|---|
| $CH_3COOH$ | 2.02 |
| $CH_3CH_2COOH$ | 1.70 |
| $CH_3CH_2CH_2COOH$ | 1.00 |
| Higher alkanoic | 1.00 average |
| $CH_3CH-COOH$<br>$\quad\vert$<br>$\quad CH_3$ | 0.67 |
| $CH_3CH_2CH-COOH$<br>$\qquad\vert$<br>$\qquad CH_3$ | 0.20 |
| $CH_3CH_2-CH-COOH$<br>$\qquad\quad\vert$<br>$\qquad\quad CH_2$<br>$\qquad\quad\vert$<br>$\qquad\quad CH_3$ | 0.02 |

The presence of an ethyl group alpha to the acid function has a stronger effect than a methyl group, and higher alkyl groups will tend to have stronger effects. Hydrolysis rates will have the same comparative order. The position of chain branching with respect to the acid function may affect the rate. In some synthetic fatty acids, various isomers are often present which differ mainly in the type of substitution alpha to the carboxy group, i.e the n-acid (no substitution, also called terminal acid) 2-methyl acid, 2-ethylacid, which causes different hydrolysis rates. For example, with methyl esters of tridecanoic acids, the relative hydrolysis rates for n-ester:2-methyl dodecanoate ester:2-ethylundecanoate ester through 2-pentyloctanoate ester are 2:1:0.5.

Synthetic fatty acids can be utilized as a substitute for coconut oil fatty acids in soaps. For such purpose it is generally important that the acids have a high normal content, and in particular that mainly terminal acids be present. Odor problems have been ascribed to non-terminal acids, and specifications may call for at least 80%, or possibly 90% or more, of terminal acid content for soap grade acids. On the other hand, for some industrial purposes, non-terminal and other branched acids are not only acceptable but their presence may be desirable. A soap grade acid of particular interest has about 15 to about 40 weight percent $C_{11}$ carboxylic acid, about 25 to about 60 weight percent $C_{12}$ carboxylic acid, and about 15 to about 40 weight percent $C_{13}$ carboxylic acid, with more than 80% of the carboxylic acids being terminal. It is also desirable that other branching in such acids be limited, such as less than 40% of the acids having other alkyl branching, or preferably less than 20% having other alkyl branching.

For industrial grade acids in the $C_{11}-C_{13}$ range, a suitable mixture may have about one-third terminal acids, one-third 2-methyl acids, and the balance 2-ethyl, 2-propyl or more highly branched acids. Such mixture may often have at least 40% or possibly at least 60% non-terminal acids.

The differential hydrolysis procedures herein may be utilized in conjunction with other procedures to prepare desired mixtures of acids or esters. Depending upon the source material, a separation by differential hydrolysis may result in one fraction suitable as soap grade material, and a second fraction suitable for industrial purposes. Of course, if necessary, either fraction can be subjected to further treatment by hydrolysis, esterification, or other procedures to obtain the desired product. The present invention provides a procedure for enriching acid mixtures with respect to terminal or branched acids.

The present procedure can be utilized for separation of any acids having different hydrolysis or esterification rates. However its most useful applications will involve acid mixtures not readily separable by other means. Thus the differential hydrolysis will be particularly useful for mixtures of acids having similar or overlapping distillation ranges.

The procedures described herein involve production of mixtures of acids and esters. Such mixtures can suitably be separated by distillation procedures in accord with art recognized procedures. The methyl and some lower alkyl esters will be of lower boiling point than the acids and can be distilled from the acids. Conversely, if higher esters are involved, it may be appropriate to distill the acid from the ester. While distillation, if applicable, will generally be the most suitable separation procedure, other acid-ester separation procedures known to the art and applicable to particular acid-ester mixtures can be employed. For example, procedures involving differential adsorption or solution can be employed, including those using ion exchange resins, such as the procedure in U.S. Pat. No. 4,125,550, for removing free fatty acids from water inmiscible fluids.

The following boiling point data is presented for use in illustrating the application of distillation, in conjunction with hydrolysis, for effecting separations. The $C_{11}$, $C_{12}$ and $C_{13}$ have reference to the number of carbon atoms in the acids.

| b.p. °C. | Internal (Range) | | | Terminal | | | |
|---|---|---|---|---|---|---|---|
| | Acids | Methyl ester | Ethyl ester | Acids | Methyl ester | Ethyl ester | n-hexyl ester |
| $C_{11}$ | 271–277 | 243 | 253 | 284 | 250 | 260 | 315 |
| $C_{12}$ | 284–290 | 258 | 268 | 299 | 262 | 273 | 338 |
| $C_{13}$ | 297–303 | 267 | 277 | 312 | 275 | 285 | 350 |

It can be seen that there is substantial overlap in the boiling ranges of the internal vs. terminal acids, viz. 271–303 compared to 284–312, and there is similar overlap in ester boiling points. However, if internal methyl esters are compared to terminal acids, the ranges are then 243–267 compared to 284–312. Thus a partial hydrolysis makes distillation a suitable method for separation. In effecting the separation, the distillation can be continued to the point where substantially all internal $C_{13}$ ester is removed, b.p. 267°. This would leave some $C_{13}$ terminal ester with the acids, where its inclusion would contribute to normality, but require hydrolysis if acid product is desired. Or the distillation can be continued to distill all ester, including $C_{13}$ terminal ester (b.p. 275°) but also removing some of the $C_{11}$ branched acids; distillation of the latter increases the normality of the residual acids. The foregoing exemplifies the type of carboxylic acid mixture especially suitable for fractionation by the present invention. Thus the original acid mixture has a molecular weight or carbon number range such that the boiling point range of the internal acids overlapped the boiling point range of the terminal acids; but the boiling point range of the internal esters did not overlap the boiling point range of the terminal acids, and in fact was well over 10 degrees different. In the event there is some overlap of the boiling range of the internal esters with that of the terminal acids, distillation may still be utilized to separate the esters and achieve some enrichment in the desired isomers, particularly if the overlap only involves a small fraction of say up to 25% or so of the mixture. Practicality in such event may depend upon the ratios of isomers and particular acids present, and the degree of enrichment needed, as well as the extent of overlap in boiling ranges.

With further regard to the $C_{11}$–$C_{13}$ acids and boiling points above, it is feasible to start with the ester mixture and first utilize distillation to remove the $C_{11}$ internal ester, and then carry out the differential hydrolysis and subsequent treatment on the residue. If this is done, the hydrolysis and subsequent separation can produce a greater enrichment in the terminal acids.

The same principles are involved in utilizing differential esterification in place of hydrolysis. The normal acids esterify at the faster rate. The resulting esters are enriched with respect to normal content while the unesterified acids are enriched in branched acids. Distillation or other procedures can be used for separation in similar manner to that following hydrolysis procedures, but recognizing that the higher normal content will be in the ester fraction.

Hydrolysis and esterification procedures are well known and are viewed as generally applicable in the present invention. The differential rates involved appear due to properties of acid moieties and to be substantially independent of particular types of procedures. Thus the particular procedures employed can be selected on the basis of overall rates, convenience, efficiency, cost, etc. without having great effect on the compositive rates of the acids involved. For large scale operations, procedures known to be effective for hydrolysis of glyceride fatty esters may be particularly suitable, and may involve temperatures of about 260° C. with resulting pressures around 700 psi gauge. Since an equilibrium reaction is involved, it is desirable to remove the alcohol formed in the reaction. Such removal can be accomplished by aqueous counter current extraction in accordance with practice in gylceride hydrolysis. When a low boiling alcohol, such as methanol, is utilized, the alcohol can be removed by vapor removal, utilizing a distillation column or the like. High conversions are obtainable by removal of the alcohol. However, in order to obtain the desired isomer enrichment, the hydrolysis will be stopped short of completion, taking about the maximum conversion obtainable with production of the desired isomer content. This will vary with hydrolysis rates, isomer ratios and desired product. However, with some fatty acid mixtures, conversions of 85 to 90% or so are feasible to produce acids of better than 85 or 90% normality, and the normality of the product then tends to drop rapidly as the conversion goes beyond 90%.

The present invention can be utilized with any mixtures of carboxylic acids and their esters exhibiting different hydrolysis-esterification rates. Alcohols in general are useful as the alcohol moiety in the esters, and the ester mixtures prepared by various procedures can be utilized, aside from what alcohol group is present in the esters. However, if an ester is being deliberately prepared for a differential separation procedure, it is often convenient to use a simple alcohol, such as methyl alcohol. The methyl esters are generally lower boiling than their carboxylic acids and can be removed therefrom by distillation. Higher alcohol esters can also be separated from their acids by distillation, but as the alcohol increases in molecular weight the boiling point increases, and beyond a certain molecular weight the acid will be distilled from the ester. Ordinarily alcohols, particularly alkanols, of 1 to 10 carbon atoms will be utilized for esterification, as there is little reason to handle additional material, but higher or other alcohols may be used and such use may be advantageous in special circumstances. Phenols can also be utilized to prepare phenolic esters of the acid mixtures and separations achieved through either differential hydrolysis or differential esterification.

Acids or bases can be used to catalyze the hydrolyses or esterifications in known manner and will generally permit faster rates at milder conditions. However such solutions tend to be corrosive and the resulting need for special equipment or procedures in commercial practice would tend to outweigh the economic advantage of lower temperature, etc.

The present invention can be utilized especially in enriching the normality of acids and esters obtained by various procedures for hydrocarboxylating or hydroesterifying olefins. For example the procedures in U.S. Pat. Nos. 2,911,422, 3,579,551 and 3,579,552 employing various cobalt, rhodium and iridium catalysts, or in procedures such as described in U.S. Pat. Nos. 3,507,891 and 3,856,832. It is contemplated that the process can be conducted utilizing a hydroesterification process in which a relatively high concentration of cobalt catalyst is utilized at elevated temperature and pressure, namely about 2.5 to about 6 weight percent of the reaction solution (calculated as cobalt); and in a subsequent phase separation, the cobalt is mainly in the aqueous phase with only very little found in the organic phase from which product can be distilled. The catalyst can be recycled to the reaction. Advantageous conditions for such hydroesterification include 180° to 200° C., 1200 to 1800 psi carbon monoxide pressure, an $H_2/CO$ ratio in the range of 0.02 to 0.05, a pyridine to cobalt molar ratio in the range of 2 to 10, and methanol to olefin molar ratio of 2 to 5. The aforesaid hydroesterification process in itself, utilizing a high cobalt concentration, including the described concentrations and conditions and recovery procedures, is hereby acknowledged as an invention of a fellow employee, Gordon T. Chen.

EXAMPLE 1

A mixture of methyl tridecanoate isomers containing 72% normal tridecanoate, 50 grams, was heated with 21 grams water at 260° C. in a 300 ml stainless steel autoclave for 30 minutes, obtaining 34% hydrolysis. The normality of the acid produced was 85%.

EXAMPLE 2

A 1 ml. amount of methyl decanoate isomers, 75% methyl n-decanoate, was placed in a Regis tube with 1 ml water and 1 drop sulfuric acid was added and the tube sealed. The procedure was repeated, and the two tubes placed in a muffle furnace at 190° C. One tube was removed after one hour, and the second after two hours, with hydrolysis results as follows

| Isomer | % Hydrolysis | |
|---|---|---|
| | One Hour: | Two Hours |
| n-decanoate | 17.6 | 47 |
| 2-methylnonanoate | 17.2 | 31.8 |
| 2-ethyloctanoate | 18.9 | 19.8 |
| other | 6.5 | 5.8 |

-continued

| Isomer | % Hydrolysis | |
|---|---|---|
| | One Hour: | Two Hours |
| Total | 17.2 | 41.9 |

Of the acid produced in the two hour sample, 89.6% was n-decanoic acid, demonstrating a marked enrichment in that isomer.

and the contents removed and permitted to phase, and the upper ester-acid phase was then separated, sampled, and returned to the reaction with a fresh charge of water. The lower water-methanol phase was discarded. In all, eight cycles were made with intermediate removal of water. A check of the pressure during the first cycle showed a pressure of 800 psi gauge. The results are reported below. The times reported are cumulative time, counting only that above 240° C., and not the rest of the heating and cooling time.

| Sample No./Time | Mole % (normalized to 100%) | | | | | | |
|---|---|---|---|---|---|---|---|
| | n-acid | 2-methyl acid | 2-ethyl to 2-pentyl acid | unknown | n-ester | 2-methyl ester | 2-ethyl to 2-pentyl ester |
| Starting ester | 3.2 | 1.5 | 2.1 | .5 | 55.2 | 21. | 16.2 |
| 1/26 min. | 28.5 | 6.1 | 4.8 | 1.6 | 29.9 | 15.2 | 13.6 |
| 2/50 min. | 45.8 | 10.6 | 6.8 | 0.9 | 14.4 | 10. | 11.5 |
| 3/72 min. | 52.4 | 14.8 | 8.3 | 2.2 | 7.0 | 6.1 | 8.7 |
| 4/92 min. | 56.5 | 17.2 | 9.6 | 2.2 | 3.9 | 3.8 | 6.6 |
| 5/114 min. | 58.6 | 18.8 | 10.7 | 1.5 | 2.5 | 2.2 | 5.2 |
| 6/140 min. | 59.2 | 19.6 | 12.7 | 1.5 | 1.2 | 1.1 | 4.6 |
| 7/162 min. | 59.9 | 20.3 | 12.9 | 1.5 | 0.8 | 0.6 | 3.6 |
| 8/186 min. | 59.4 | 20.4 | 14.3 | 1.5 | 0.4 | 0.4 | 2.8 |

EXAMPLE 3

Hydrolysis procedures were carried out in Regis tubes as described in Example 2 but utilizing a mixture of 0.5 ml of methyl decanoate isomers (75% normal) and 0.5 ml of methyl tridecanoate isomers (65% normal). Three tubes were prepared and heated for 1, 2 and 3 hours respectively with results as follows with respect to degree of hydrolysis of the esters and normality of the acids produced:

| Time | % Hydrolysis | | | | % Normality of Acid | |
|---|---|---|---|---|---|---|
| | $C_{10}$ | n-$C_{10}$ | $C_{13}$ | n-$C_{13}$ | $C_{10}$ | $C_{13}$ |
| 1 hr. | 24 | 28.1 | 24.9 | 28.9 | 84.8 | 85.6 |
| 2 hrs. | 29.2 | 32.5 | 30.8 | 33.8 | 85.7 | 88.2 |
| 3 hrs. | 27.5 | 31.5 | 26.6 | 29.8 | 84.3 | 88.6 |

EXAMPLE 4

A mixture of methyl tridecanoate isomers, 95% pure and containing 65% methyl n-tridecanoate, was subjected to partial hydrolysis under basic conditions. A 10 ml amount of the isomer mixture was placed with 10 ml water in a flask equipped with a reflux condenser, along with 0.15 gram sodium hydroxide. The mixture was heated to reflux with stirring. After forty minutes, a sample was taken from the organic phase and a sodium tridecanoate white crystalline solid formed therein upon cooling. The sample was acidified with sulfuric acid and solids were separated by filtration and washed three times with water. By gas chromatographic analysis it was determined that the material was 64.9% hydrolyzed, and that 97.5% of the tridecanoic acid was n-tridecanoic acids, representing a substantial enrichment from the original 65%.

EXAMPLE 5

A 300 ml. stainless steel, stirred autoclave was utilized as reactor and initially charged with 51.2 grams methyl tridecanoate isomers (60% normal), 36 grams water (0.7 gram water/gram ester) and 8.7 grams tridecane (as an internal standard for gas chromatographic analysis). The reactor was heated to about 260° C., operated for a recorded time (15-20 minutes) cooled, The above procedure simulates a continuous counter current liquid-liquid extraction procedure of the type commonly employed in glyceride fatty ester hydrolysis. In that type of reactor water is fed countercurrent to the fatty ester in large enough excess to form a second liquid phase, and pressure is maintained high enough to keep the water as a liquid operating temperature. Long chain methyl esters require about the same operating temperatures as glyceride esters, about 250° C. or higher being appropriate for good conversion rates. The above results indicate that the procedure can be employed for differential hydrolysis and separation of the isomeric acid esters. It is apparent that the n-ester hydrolyzes at an appreciably faster rate than the other isomers, and that the resulting acids are enriched in normal content.

By plotting the data it is concluded that the n-ester is 98% converted in 2-hours, the 2-methyl ester 98% converted in 3 hours, and other internal esters are only 80% converted after 3 hours.

EXAMPLE 6

The autoclave of Example 5 was charged with 50 grams methyl tridecanoate isomers (72% normal) and 21 grams water (weight ratio 0.42 gm $H_2O$/gm ester). The autoclave was heated to 260° C., and run through five cycles with separation from the aqueous phase and returned to the reactor with a fresh charge of water, as in Example 5. Results were as follows:

| Time at Reaction Temperature-hrs. | %Conversion of Ester Isomers | | | | n-acid content of acid |
|---|---|---|---|---|---|
| | 2-ethyl to 2-pentyl | 2-methyl | n | Total | |
| 0 | — | 3 | 4 | | — |
| ½ | 10 | 22 | 35.4 | 34 | 85 |
| 1 | 36 | 56 | 62 | 61 | 79 |
| 1½ | 50 | 69 | 73 | 72 | 78 |
| 2 | 69 | 84 | 86 | 84 | 77 |
| 2½ | 76 | 90 | 92 | 90 | 77 |

The relative ratio of the first order rate constants of the hydrolysis during the initial state was n-ester:2-methyl ester:2-ethyl to 2-pentyl ester = 1:0.55:0.34. The rate of disappearance of the n-ester was little more than one-half that of Example 5 where a higher ratio of water to ester was employed, suggesting that the reverse reaction is occurring to a significant extent. Additional water might increase the rate further; in addition, if the n-ester hydrolysis was being significantly inhibited by equilibrium while that of the internal esters was not, selective hydrolysis could be further enhanced by appropriate water concentrations.

EXAMPLE 7

An initial charge to the reactor was made of 76.4 grams methyl tridecanoate isomers (65% normal) and 19 ml water and the reactor was heated to 260° C., and provision was made for removal of vapor. Initially there was insufficient water to effect good vapor removal, and the total pressure was about 300 psi gauge. Additional water was pumped and the pressure held constant at 650 psi gauge by a back pressure regulator as vapor was removed. Water was added in quantity equal to the vapor condensate collected (water, methanol and small quantity ester/acid). The hydrolysis occurred at good rates with the normal ester hydrolyzing more rapidly than the internal esters. In the initial stage water was added at 18 ml per hour, and at the rate of 210 ml per hour in the latter stage of the approximately 100 minute reaction time. From the results the initial first order rate constants were calculated, in hours$^{-1}$, as n-ester: 2-methyl ester:2-ethyl to 2-pentyl esters=0.4:0.2:0.13, and in the final stage as 6:3:2.

EXAMPLE 8

An 80 ml quantity of methyl tridecanoate isomers was charged to a stainless steel autoclave with 3% by weight sulfonic acid resin, 12 ml tridecane, 12 ml octanal, and water in 5:1 mole ratio to the ester. The reactor was heated to 180° C. with stirring at 1000 rpm. In one hour 8% hydrolysis occurred with a relative rate of 2.4:1 of normal to internal esters. Corrosion of the reactor was noted.

EXAMPLE 9

N-hexyl tridecanoate isomers were heated in a Regis tube with 2% by weight sulfuric acid and a 12:1 ratio of water to ester, to a temperature of 150° C. to produce 10% hydrolysis in 2 hours. The relative rate of hydrolysis of normal to internal ester was 1.9.

EXAMPLE 10

Methyl tridecanoate isomers, 80 ml, 12 ml tridecane, 12 ml decanal, 0.2 weight percent $SnC_2O_4$ and water in 5:1 mole ratio to ester were heated in an autoclave to 200° C. for 30 minutes to produce 25% hydrolysis with relative rate of hydrolysis of normal to internal esters of 2.6.

EXAMPLE 11

Methyl tridecanoate isomers, 3 ml, 3 ml of acetic acid, 1 weight percent concentrated sulfuric acid and water in 12:mole ratio to ester were heated to 150° C. in a sealed 15 ml. Carius tube for 18 hours to produce 79.5% hydrolysis. The resulting acid has 88% n-acid content, compared to 81.2% normal content in the starting ester.

What is claimed is:

1. A method of separating alkanoic acids and esters having differences in chain structure in which a hydrolysis-esterification system is employed in which conditions are provided so as to cause either hydrolysis or esterification thereby increasing the concentration of one of such components and then separating at least one of alkanoic acid and ester from the reaction mixture before the hydrolysis or esterification is completed and while both ester and alkanoic acid are present in such reaction mixture.

2. A method of separating alkanoic acids with respect to linearity of structure which comprises providing a mixture of such acids in ester form, subjecting such mixture to hydrolysis to effect a partial hydrolysis of the esters in said mixture with a higher percentage of the more readily hydrolyzed esters being hydrolyzed than of the less readily hydrolyzed esters, and separating the esters from the resulting acids.

3. The method of claim 2 in which the esters are of lower boiling point than the acids and separable by distillation.

4. The method of claim 2 in which the acids include acids over a range of molecular weights.

5. The method of claim 2 in which the acids include a mixture of $C_{11}$ to $C_{13}$ carbon atom acids.

6. The method of claim 2 in which the acids in ester form are a mixture of esters produced by hydroesterification of olefin feed stock and having a normal acid content no greater than about 80%.

7. The method of claim 6 in which methyl esters are employed.

8. The method of preparation and separation for obtaining separate high and low normal content fractions of carbonylation products which comprises hydroesterifying a mixed olefin feed containing both linear and branched molecules and varying in molecular weight over at least a three-carbon range by reacting such olefin feed with carbon monoxide and alcohol over a catalyst at elevated temperature and pressure hydroesterification conditions to obtain a hydroesterification product, and subjecting such hydroesterification product to partial hydrolysis thereby hydrolyzing more of the normal esters than of the branched esters, and separating the esters from the resulting acids to provide acids having enriched content of normal acids and esters enriched in content of branched esters.

9. The method of claim 8 in which the esters are then separately hydrolyzed to acids.

10. The method of claim 8 in which the olefins are principally in the 10 to 12 carbon atom range and the esters are removed from the acids by distillation.

11. The method of claim 10 in which the bulk of the eleven carbon atom branched ester in the carbonylation product is removed by distillation prior to subjecting the carbonylation product to hydrolysis.

12. The method of claim 4 in which the acids include acids having overlapping boiling ranges.

13. The method of claim 12 in which the boiling range of internal esters present does not overlap the boiling range of the terminal acids produced.

14. The method of claim 2 in which alcohol is removed during hydrolysis to permit higher conversion of ester.

15. The method of claim 2 in which the conversion is in the range of about 80 to about 95%.

16. The method of claim 5 in which normality of acids in $C_{11}$ to $C_{13}$ ester mixtures containing less than 80% of normal acids is increased by at least 5% and with production of more than 80% normal content.

* * * * *